United States Patent
Martikka et al.

(10) Patent No.: US 11,766,214 B2
(45) Date of Patent: Sep. 26, 2023

(54) WEARABLE SPORTS MONITORING EQUIPMENT AND METHOD FOR CHARACTERIZING SPORTS PERFORMANCES OR SPORTSPERSONS

(71) Applicant: Suunto Oy, Vantaa (FI)

(72) Inventors: Mikko Martikka, Vantaa (FI); Heikki Nieminen, Vantaa (FI); Kimmo Pernu, Vantaa (FI); Olli-Pekka Ojanen, Vantaa (FI); Erik Lindman, Vantaa (FI)

(73) Assignee: Suunto Oy, Vantaa (FI)

( * ) Notice: Subject to any disclaimer, the term of this patent is extended or adjusted under 35 U.S.C. 154(b) by 499 days.

(21) Appl. No.: 14/941,736

(22) Filed: Nov. 16, 2015

(65) Prior Publication Data
US 2016/0143579 A1 May 26, 2016

(30) Foreign Application Priority Data

Nov. 19, 2014 (FI) ...................................... 20146009
Nov. 19, 2014 (GB) ...................................... 1420550

(51) Int. Cl.
*A61B 5/00* (2006.01)
*A61B 5/0205* (2006.01)
*A61B 5/0245* (2006.01)
*A61B 5/318* (2021.01)

(52) U.S. Cl.
CPC ............ *A61B 5/486* (2013.01); *A61B 5/0205* (2013.01); *A61B 5/0245* (2013.01); *A61B 5/0006* (2013.01); *A61B 5/318* (2021.01); *A61B 5/4866* (2013.01); *A61B 5/681* (2013.01); *A61B 5/6805* (2013.01); *A61B 5/6807* (2013.01); *A61B 5/6898* (2013.01); *A61B 5/7246* (2013.01); *A61B 5/7257* (2013.01); *A61B 5/7278* (2013.01); *A61B 2503/10* (2013.01); *A61B 2505/09* (2013.01); *A61B 2562/0219* (2013.01); *A61B 2562/0247* (2013.01)

(58) Field of Classification Search
CPC ...... A61B 5/486; A61B 5/0205; A61B 5/0245
See application file for complete search history.

(56) References Cited

U.S. PATENT DOCUMENTS

| | | | | |
|---|---|---|---|---|
| 4,898,182 A | * | 2/1990 | Hawkins ................ | A61B 5/222 600/509 |
| 6,013,007 A | * | 1/2000 | Root .................. | A63B 24/0006 482/8 |
| 6,450,967 B1 | * | 9/2002 | Wu ........................ | A61B 5/222 600/485 |
| 8,945,017 B2 | | 2/2015 | Venkatraman ....... | A61B 5/0205 600/500 |
| 8,961,185 B2 | | 2/2015 | Bleich et al. | |
| 9,737,761 B1 | * | 8/2017 | Sivaraj .................. | G16H 40/63 |
| 2004/0186387 A1 | | 9/2004 | Kosuda et al. | |
| 2005/0245792 A1 | * | 11/2005 | Weyand ................ | A61B 5/221 600/300 |
| 2007/0061105 A1 | | 3/2007 | Darley et al. | |
| 2007/0276200 A1 | * | 11/2007 | Ahola ................ | A61B 5/02438 600/300 |
| 2009/0043531 A1 | | 2/2009 | Kahn et al. | |
| 2009/0082681 A1 | | 3/2009 | Yokoyama et al. | |
| 2010/0125188 A1 | | 5/2010 | Schilling et al. | |
| 2010/0298655 A1 | | 11/2010 | Mccombie et al. | |
| 2011/0125188 A1 | | 5/2011 | Goraltchouk et al. | |
| 2013/0023739 A1 | * | 1/2013 | Russell ................ | A61B 5/0205 600/301 |
| 2013/0053653 A1 | | 2/2013 | Cuddihy et al. | |
| 2013/0110265 A1 | | 5/2013 | Rahko et al. | |
| 2013/0171599 A1 | | 7/2013 | Bleihch et al. | |
| 2014/0213858 A1 | * | 7/2014 | Presura .................. | A61B 5/681 600/301 |
| 2014/0275854 A1 | | 9/2014 | Venkatraman et al. | |
| 2014/0276127 A1 | | 9/2014 | Ferdosi et al. | |
| 2015/0273313 A1 | * | 10/2015 | Chen .................. | A61B 5/02405 700/91 |

(Continued)

FOREIGN PATENT DOCUMENTS

| | | |
|---|---|---|
| EP | 2407217 A2 | 1/2012 |
| EP | 2469436 A2 | 6/2012 |
| WO | WO2009021147 A1 | 2/2009 |

(Continued)

OTHER PUBLICATIONS

Lamberts, R. P. et al; "Heart Rate Recovery as a guide to monitor fatigue and predict changes in performance parameters"; Scan J Med Sci Sports (2009), vol. 20, Issue 3, p. 1-9.*
Chen, Y. K.; et al "Re-defining the roles of sensors in objective physical activity monitoring"; Med Sci Sports Exerc. Jan. 2012; 44(1 suppl 1): S13-S23 (Year: 2012).*
Conconi, F. et al; Determination of the anaerobic threshold by a noninvasive field test in runners; J Appl Physiol Respi Environ Exerc Physiol. Apr. 1982; 52(4): 869-73. (Year: 1982).*
Erdogan, A. et al; "Non-Invasive Indices for the Estimation of the Anaerobic Threshold of Oarsmen"; The Journal of International Medical Research (2010); 38:901-915 (Year: 2010).*

(Continued)

*Primary Examiner* — Jerry Lin
(74) *Attorney, Agent, or Firm* — Laine IP Oy

(57) ABSTRACT

The invention concerns wearable electronic devices, systems and methods for sports performance monitoring. In one embodiment, the invention provides a device comprising a heartbeat sensor for providing a heartbeat signal, a motion sensor for providing a motion signal and processing means adapted to calculate at least one performance parameter depicting said sports performance and/or the person using temporal characteristics of periodic features of the heartbeat signal compared with temporal characteristics of periodic features in the motion signal. The invention allows for utilization of an existing relation between cadence and heart rate for characterizing the performance or the person in a novel way.

20 Claims, 11 Drawing Sheets

(56) References Cited

U.S. PATENT DOCUMENTS

2016/0143544 A1* 5/2016 Tanaka ................ A61B 5/0015 600/479
2016/0361020 A1* 12/2016 LeBoeuf .............. A61B 5/7278

FOREIGN PATENT DOCUMENTS

WO   WO2014120831 A1   8/2014
WO   WO2016069082 A1   5/2016

OTHER PUBLICATIONS

Droghetti, P. et al.; "Noninvasive determination of the anaerobic threshold in canoeing, cross-country skiing, cycling, roller, and iceskating, rowing, and walking". Europ. J. Appl. Physiol. 53, 299-303 (1985). (Year: 1985).*

Ainslie, P.N. et al.; "Estimating Human Energy Expenditure"; Sports Med 33, 683-698 (2003). (Year: 2003).*

Strath, S. J. et al; "Validity of the simultaneous heart rate-motion sensor technique for measuring energy expenditure", Medicine & Science in Sports & Exercise: May 2002; vol. 34; Issue 5; p. 888-894. (Year: 2002).*

Freedson, P.S. et al; "Objective Monitoring of Physical Activity Using Motion Sensors and Heart Rate"; Research Quarterly for Exercise and Sport; Jun. 2000; 71, 2, p. 21-29. (Year: 2000).*

Weltman, A. et al; "Reliability and Validity of a Continuous Incremental Treadmill Protocol for the Determination of Lactate Threshold, Fixed Blood Lactate Concentrations, and VO2max"; Int J Sports Med 1990; 11(1): 26-32. (Year: 1990).*

Nichols, J. F. et al; "Relationship Between Blood Lactate Response to Exercise and Endurance Performance in Competitive Female Master Cyclists", Int. J. Sports Med., (1997) vol. 18, pp. 458-463. (Year: 1997).*

Wang, Y. et al. "A Layered Reference Model of the Brain." Proceedings of the Second IEEE International Conference on Cognitive Informatics (ICCI'03), 2003, pp. 1-11 (Year: 2003).*

Cook, D.A. et al. "Accuracy of Physicians' Electrocardiogram Interpretations: A Systematic Review and Meta-analysis". JAMA Intern Med. 2020;180(11):1461-1471 (Year: 2020).*

Hatala, R.M. et al. "Practice makes perfect: the critical role of mixed practice in the acquisition of ECG interpretation skills." Advances in Health Sciences Education 8.1 (2003): 17-26 (Year: 2003).*

* cited by examiner

WEARABLE SPORTS MONITORING EQUIPMENT AND METHOD FOR CHARACTERIZING SPORTS PERFORMANCES OR SPORTSPERSONS

FIELD OF THE INVENTION

The invention relates to a wearable electronic devices and systems for monitoring sports performances. In particular, the invention relates to a solution for characterizing a sports performance using heartbeat and motion data collected during a performance. More specifically, the invention provides a device or multi-device system comprising a heartbeat sensor, a motion sensor and a processing unit for processing data provided by the sensors. The invention also provides an associated method.

BACKGROUND OF THE INVENTION

Heart rate sensors are commonly used for monitoring and characterizing sports performances. Most commonly, they are based on electric measurement of heart activity using electrodes placed on the skin of a person, i.e. using an electrocardiographic (ECG) measurement. Heart rate can be determined by detecting individual heartbeats from the ECG signal and counting their frequency. Heart rate as such is an important characteristic parameter of the performance but it can also be used to estimate for example energy consumption of the person. This is also very common in existing sports monitoring equipment.

Heart rate as such, i.e. without further information, does not give almost any indication on the fitness level of the person or the strain level (power) of the ongoing performance, such as energy consumption or training effect, to mention some typical performance parameters of interest. A professional athlete, for example, utilizes energy more efficiently than an irregular trainee. On the other hand, if the fitness or strain level is known, the other can be estimated based on the heart rate. There is, however, the problem that in many cases neither of them is reliably known. Of course, a subjective estimate of the user may be utilized as input, but this is prone to large errors and/or continuous updating as the training proceeds.

Acceleration sensors are commonly used to count for example steps during running, revolutions during cycling or strokes during swimming, or frequencies thereof (i.e. cadence) but they do not give direct information on the intensity of the performance or fitness of the person. Direct power level measurements, on the other hand, require special instrumentation and are only applicable to some typically indoor exercises and equipment, such as rowing machines or fitness bicycles. Besides that, they can measure directly only a portion of consumed energy which is transferred into mechanical energy, whereby the problem relating to "physiological economy" remains.

Yet another challenge is that the heart rate follows the intensity changes with delay. Therefore relating heart rate based information to for instance acceleration sensor based information is challenging. Current algorithms solve this by searching for situations where heart rate is stabilized. However, in sports where the intensity is changing a lot, like in tennis, soccer, and floorball, these calculations usually fail.

Thus, there is a need for improved methods for determining performance parameters, in particular relating to training intensity and strain and fitness level.

SUMMARY OF THE INVENTION

It is an aim of the invention to provide a novel solution for characterizing sports performances. A particular aim is to provide novel equipment that is able to determine a performance parameter depicting for example the intensity of the sports performance, strain of the performance on the person and/or fitness level of the person in a way that utilizes heartbeat data and motion data measured during the performance in a novel manner giving more information for the user on his/her training session and/or physical condition than previously available devices or systems.

A further aim is to provide a corresponding method for characterizing a sports performance.

A particular aim is to provide equipment and method that are capable of meeting the at least part of the abovementioned goals when the intensity level or the performance changes a lot.

According to one aspect, the invention is based on estimating the anaerobic threshold level of the person based on the deviation in the frequencies of the rhythmic movements of the user (i.e., cadence) and heartbeat (i.e., heart rate). That is, temporal correlation between periodic features of heartbeat signal and for example acceleration signal measured from the user are used to determine a performance parameter descriptive of the particular person, the performance carried out or both. The output can be selected from a variety of performance parameters known per se in sports monitoring applications or completely new ones. Examples include for example fitness level of the person and/or intensity of the performance or strain caused by the performance. Fitness level can be given as anaerobic heart rate threshold level or a fitness index, intensity as energy consumption, power or speed and strain level as a fatigue index, such as EPOC (Excess Post-exercise Oxygen Consumption) or energy consumption. Alternative potential performance parameters include maximal proposed step length or proposed maximal running speed in aerobic range. The determination of various specific performance parameters are described later in more detail.

In further details, the invention provides sports monitoring equipment comprising a heartbeat sensor for providing a heartbeat signal and a motion sensor for providing a motion signal. In addition, there are provided processing means adapted to compare the temporal characteristics of the signals and to calculate at least one performance parameter based on this comparison. In particular, the processing means are adapted to calculate at least one correlation factor dependent on temporal characteristics of periodic features of the heartbeat signal compared with temporal characteristics of periodic features in the motion signal, and to calculate at least one performance parameter depicting said sports performance and/or the person using said correlation factor. In one preferred embodiment, the processing means is configured to implement a mathematical relation between the frequencies of the heartbeat and cadence and further to use that relation to the characterize the performance or the person, most advantageously the intensity or strain of the performance, fatigue of the person and/or the fitness level of the person.

The method according to the invention comprises measuring heartbeat of the person using a wearable heartbeat sensor for providing a heartbeat signal, measuring movement of the person using a wearable motion sensor for providing a motion signal. The method further comprises analyzing the heartbeat signal detecting periodic features in the heartbeat signal and in the motion signal, determining temporal correlation of the periodic features of the heartbeat signal and the motion signal, and calculating at least one performance parameter based on said temporal correlation determination. The analysis and calculations are carried out in one or more computing units functionally connected to the wearable heartbeat sensor and the wearable motion sensor. According to a preferred embodiment, the performance parameter depicts intensity of the sports performance, strain of the performance, fatigue of the person and/or fitness level of the person.

More specifically, the invention is characterized by what is stated in the independent claims.

The invention provides considerable advantages. It has been found that motion characteristics in relation to heartbeat characteristics provide information on the performance that has not been used before. In particular, since the comparison of heart rate and cadence in rhythmic performances such as running gives information on metabolism of the person during the performance, it can be used to characterize his/her fitness level or the performance itself. A typical example of characterization is accurate determination of fitness level of the person. By means of the invention, this can be done robustly without complex measurements, such as respiration measurements. A more advanced example of characterization is the optimization of intensity of a sportsman so that he is able to complete a planned performance with maximum pace. In other words, the invention suits for performance efficiency optimization. Further advanced embodiments of the invention utilize combined speed and/or step length determination, which give further data to be used in the characterization of the person or the performance. One example is the monitoring of the fitness level of the person using the information that at the anaerobic threshold, the speed is dependent mainly on the step length. That is, if the person is able to continue for a longer time at or close to the anaerobic threshold or is able to a run a longer distance in a given time at or close to the threshold, he/she is probably in a better shape than before.

The invention described above can be used to determine fitness level of the person accurately. When the fitness level is known, heart rate value can be converted to accurate energy consumption estimate. On the other hand, energy consumption estimate of the eerformance can be achieved also from other sources, such as from speed measurement with conversion or directly from power sensors, for instance a bike power sensor. When these energy consumption estimates are received from several sources, more information on person's metabolism and fitness level can be extracted.

The invention is very well suited for characterizing running performances, but besides that, it can be directly used to characterize other rhythmic sports, such as walking and cycling, where there is a relation between cadence and heart rate (or more generally speaking between temporal characteristics of motion and heartbeat) which can be expressed as a mathematical function in a suitable way. In addition, once the fitness level of the person is known, the results obtained by means of the invention can be used in characterization of practically any sports performances. For example, fitness level of the person obtained by means of the invention during a running performance can be used as an input parameter in energy consumption calculation algorithm designed for any sports.

Computational operations necessitated by the invention are relatively simple to implement in modern microcontrollers or processors and consume only a minor amount of energy. Thus, the invention can be well implemented in wearable battery-operated devices.

The dependent claims are directed to selected embodiments of the invention.

According to one embodiment, the processing means are adapted to determine heart rate using the heartbeat signal and frequency of periodic features of the motion signal, in particular acceleration signal. The correlation factor is designed to be sensitive to (i.e., is dependent on) the difference between the heart rate and frequency of the periodic features of the acceleration signal. The difference, including its sign, reflects the present metabolic state of the person and intensity of the person. Heartbeat and motional frequencies can be determined in frequency domain by calculating a Fourier transformation of the heartbeat and acceleration signals and to compare frequency characteristics of the signals in the frequency domain. The frequency characteristics comprise in particular the heart rate and the most dominating frequency component of the motion signal, typically corresponding to cadence. Alternatively, the necessary operations can be carried out in the time domain.

According to one embodiment, the processing means is adapted to detect individual heartbeats from the heartbeat signal and to associate first time stamps with the individual heartbeats, and to detect periodic movements of the person relating to the sports performance from the acceleration signal and to associate second time stamps with the periodic movements. The first and second time stamps are then utilized for calculating the correlation factor. This method is computationally lightweight and efficient to implement in wearable microcontroller-operated devices in particular. In one further embodiment, the microcontroller or other processing means used is adapted to detect and/or estimate, using said first and second time stamps, the frequency of heartbeats at which the temporal difference between the individual heartbeats and temporally related individual movements remains essentially constant over a plurality of periods of the signals. This frequency roughly corresponds to the anaerobic threshold heart rate of the person and can be used as such as the performance parameter according to the invention. Alternatively or in addition to that, the performance parameter may comprise present deviation from anaerobic heart rate threshold level, present power level of the performance, energy consumption or training effect.

In one embodiment, the correlation factor is proportional to the ratio of the heart rate and cadence determined based on the signals measured. In this case, the performance parameter may be the ratio itself or an index number describing the ratio.

One example of the usage areas of the invention is to follow changes in the metabolism of the person due to increasing load of the performance. When the intensity of the performance changes, the heart rate and heart rate related parameters follows this intensity change with delay. When the load increases the heart rate and heart rate related parameters response time to intensity change increases. This means that changes in time delay, relative to resting condition, correlate with real time EPOC and thus describe fatigue level of the person.

According to one embodiment, the processing means are adapted to compute, based on the heartbeat signal and motion signal, a time delay parameter depicting delay between response of the heartbeat signal to intensity changes in the performance and response of the motion signal to intensity changes in the performance. Then, it is able to compute the performance parameter, in this case most advantageously fatigue index, such as EPOC, by observing changes in the time delay parameter during the performance. This is because changes in the time delay parameter defined this way reflect the individually experienced fatigue level of the performance essentially in real time during the performance.

In one embodiment, the processing means are adapted to determine the a first value of the abovementioned time delay parameter when the person is at a resting state (with resting heart rate, e.g. prior to the actual performance) and a second value of the time delay parameter during the performance (with elevated heart rate) and to compute the fatigue index using a mathematical function, such that a linear or partially linear function, dependent on the first value and the second value.

Generally speaking, the time delay parameter can be quantified accurately at all times only when correlation between the heart rate based and physical intensity related parameters can be mathematically formulated. In this mathematical formulation finding accurate fitness index and mathematical formulation for time delay are of particular importance. A detailed calculation example is given later in this document.

According to one embodiment, which is somewhat reverse to the one described above, the processing means are adapted to read a predetermined time delay parameter depicting delay between response of the heartbeat signal to intensity changes in the performance compared and response of the motion signal to intensity changes in the performance, and to compute the performance parameter using the heartbeat signal, motion signal and the time delay parameter. Instead or in addition to a single value of the time delay parameter, a predefined behavior model of the parameter on intensity changes can be used. In this case, the performance parameter is in particular fitness index, which can in this way be calculated even if the performance comprises a lot of intensity changes. This embodiment is particularly advantageous if the user starts the performance when fully rested (recovered from previous exercises). Knowledge of the time delay parameter and/or behavior thereof sufficient for determining the fitness index during performance can be obtained from an orthostatic heart rate test carried out by the person prior to the performance.

According to one embodiment, the equipment comprises a means for determining the speed of the person. These means may comprise for example a position measurement device, such as a satellite positioning sensor, or the accelerometer of the device can be used for speed determination, in particular with known step or revolution length. In addition, the magnetometer or gyroscope can be used alone or in combination with accelerometer to determine speed. The processing means is adapted to determine the speed from sensor input data and to utilize the speed together with the correlation analysis for calculating the performance parameter.

According to one embodiment usable for monitoring running performances, there are provided means for determining an average step length of the person and the processing means are further adapted to utilize said average step length for calculating the performance parameter. There are various options for determining the average step length. For example, the equipment may be configured to read the step length as a user-input parameter from a memory of the equipment, and/or determine the step length based on the acceleration signal only, and/or determine the step length based on the combination of the periodicity of the acceleration signal and speed data obtained using a position sensor.

The parts and functionalities in accordance with the invention may be provided in a heart rate measurement module, wristop computer, mobile phone or a system comprising two or more of these separate devices having a communication link between them. According to one embodiment, there is provided at least an electric heart rate module integral with or functionally connectable with a heart rate belt or smart garment with integral heart rate measurement electrodes so as to form said heartbeat sensor. The module may optionally comprise also the acceleration sensor and further optionally at least part of said processing means. Thus, part of all of the essential measurements can be carried out in a single module, as well as also part or all of the computing operations.

According to one embodiment, there is provided a wristop computer or mobile phone capable of wirelessly communicating with an electric heart rate module for receiving said heartbeat signal and/or acceleration signal and/or data processed in the module using such signals, and comprising at least part of the processing means. In this embodiment, there is preferably a wireless data link from the heart rate module to the wristop computer for providing the desired data essentially in real time for further processing.

In one particular embodiment, there is provided at least one displayless electric heart rate module integral with or functionally connectable with a heart rate belt or smart garment with integral heart rate measurement electrodes so as to form said heartbeat sensor, and the module comprising said acceleration sensor and at least part of said processing means. In addition, there is provided a wristop computer or mobile phone capable of wirelessly communicating with the displayless electric heart rate module and provided with display for visualizing said performance parameter. Instead of performing only a part of the processing in the displayless device, it may also perform it all and only transfer the results of the calculation to the wristop computer or mobile phone for storage and/or visualization.

The processing means may comprise a processing unit located in a single device unit or two or more separate processing units of different device units, depending on the overall equipment architecture. Examples of architecture include a single device unit being a heart rate measurement module part of or attachable to a garment or a wrist-worn unit comprising integrated sensors, and a distributed device model with two or more device units in wireless communication link with each other.

The processing unit(s) referred herein and contained in the one or more device units may comprise a data processor of any kind, in particular a microcontroller or a microprocessor together with potentially required related components, such as memory components (e.g. RAM, ROM) and input/output circuits functionally connected thereto. In the distributed device model, two or more processing units located in two or more device units and programmed to carry out different parts of the present method together form the processing means.

According to one embodiment, the heartbeat sensor comprises a pair of ECG electrodes positionable against the skin of the person for providing the ECG signal. According to alternative embodiments, the heartbeat sensor comprises an optical sensor, a pressure sensor or an acceleration sensor. Thus, instead of electrically detectable cardiographic response, the sensor may be sensitive for example to optically detectable cardiovascular changes due to heartbeats, cardiovascular pressure changes due to heartbeats or cardiovascular-induced motion detectable on the surface of skin.

The location of the heartbeat sensor during the performance may be chest, waist, neck, wrist, upper arm or auricle, to mention some examples.

Some additional embodiments relate to utilization of the motion signal for determining the type of sports in particular for changing the energy consumption algorithm used and and for filtering motion-induced artifacts from the heartbeat signal. These embodiments are introduced in more detail later.

Definitions

"Cadence" means the frequency of repetitive motor movements. As concern running, it means herein the frequency of a single foot touching the ground. If measured using an acceleration sensor positioned at one foot or arm, the main frequency of the signal gives the cadence directly. If measured from using a sensor at the chest, twice the cadence is typically obtained (as the torso is bounced at every step). As concerns cycling, cadence means the feet revolution frequency and so on. Typically, cadence is expressed in units 1/min (e.g. steps or revolutions per minute).

"Comparing" of temporal characteristics of the heartbeat and motion signals means forming any mathematical function dependent on temporal characteristics, such as frequency, derived from the two signals. In particular, the mathematical function may comprise the difference or ratio of heart rate and cadence. The function can also be comprise any other function descriptive of the temporal correlation of these or other periodic features found in the signals.

The term "performance parameter" herein means any value characteristic to the performance being monitored and/or the person carrying out the performance. In particular embodiments, the term refers to intensity of the sports performance and/or fitness level of the person. "Intensity of performance" refers to any quantity, which correlates with the metabolic energy required and/or mechanical produced in the performance. "Fitness level of person" refers to any quantity, which correlates with the physical condition of a person and being determinable utilizing the data measured. As understood, both these quantities are even at best estimations.

The term "type of sports performance" refers mainly to different sports necessitating different kinematic (motor) behavior, such as motor functions and/or temporal activity. In simplest form of the invention, there are only two types that need to be distinguished: rhythmic (or cyclic) and non-rhythmic (irregular) sports. However, this separation can also be finer. Thus, there may also be three or more types, for example intermediate types between and/or subtypes in each main type. The threshold(s) between the types need to be selected to correspond with the variety of sports the equipment is intended to be used in, also keeping an eye on the energy consumption algorithms chosen to be used. In technical level, the type of the sports performance is typically represented by a suitable computer-readable variable in a memory device. The type variable is configured to take a value out of a plurality of values the number of which depends on the number of types available.

The terms "rhythmic" and "rhythmicity" refer to behavior (of performance/signal) having a relatively constant frequency (of successive motions/characteristic signal features). In other words, in "rhythmic" sports performance, similar body motions are repeated one after another at constant intervals. This results in a motion-sensitive signal with detectably similar signal characteristics at constant intervals. In irregular performances, either the body motions or their repeat intervals, typically both, are not similar from one to another. This results in a motion signal with more randomness. Rhythmicity can be characterized for the purposes of some embodiments of the invention using correlation or Fourier analysis, for example.

The term "wearable equipment" covers all mobile devices and multi-device systems, which are designed or can otherwise to be attached to one or more body parts directly or via a piece of clothing, including various kinds of shirts, jackets, pants and shoes, for example, or wearable accessory, such as a wearable mobile phone arm holder. Single wearable devices include in particular wristop computers, mobile phones, heart rate belts, smart garments and sensor units of various kinds, such as ECG and EMG measurement modules, satellite positioning units, acceleration measurement units (foot and arm "pods"), providing some or all of the functionalities as herein described. In other words, the invention covers individual self-contained units providing the necessary functionalities of the invention and as well as systems formed of a plurality of separate units capable of communicating with each other so as to form an operational entity providing said functionalities.

Unless otherwise mentioned, references to a "heart rate belt" and "smart garment" include the option that the belt or garment contains, in addition to an integral heartbeat sensor, an integral computing and communication unit (hereinafter: processing unit) and the option that the computing and communication unit is mountable to the belt or garment as a releasable module in functional connection with the heartbeat sensor. The other way round, the term "module" may equally refer to an integral module in a heart rate belt or smart garment or a removable module functionally connectable with a belt or garment.

"Reading" an (ECG or motion) signal covers direct measuring of the signal in a device but as well receiving the signal from another device over a wireless link, for example. As discussed above, the invention can be provided in the form of a system comprising one or more wearable sensor devices and a main processing unit in distributed configuration.

Next, embodiments and advantages of the invention are described in more detail with reference to the attached drawings.

DETAILED DESCRIPTION OF EMBODIMENTS

Figure 1A:
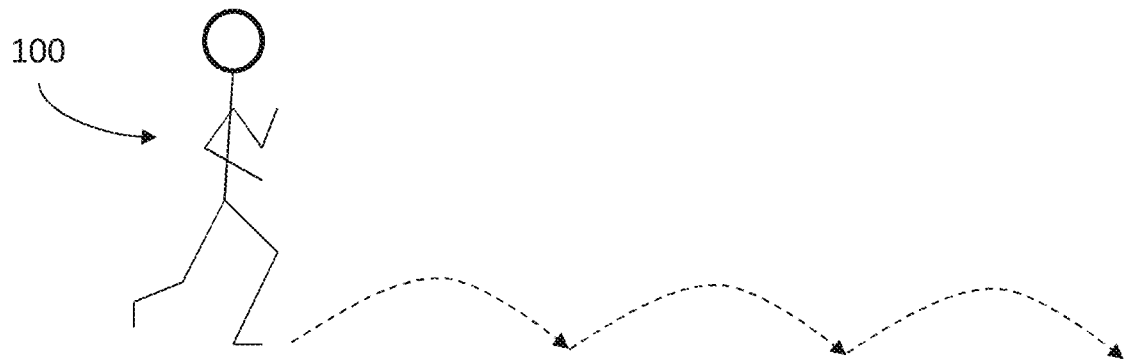
FIG. 1A depicts a runner and his cadence.
Figure 1B:
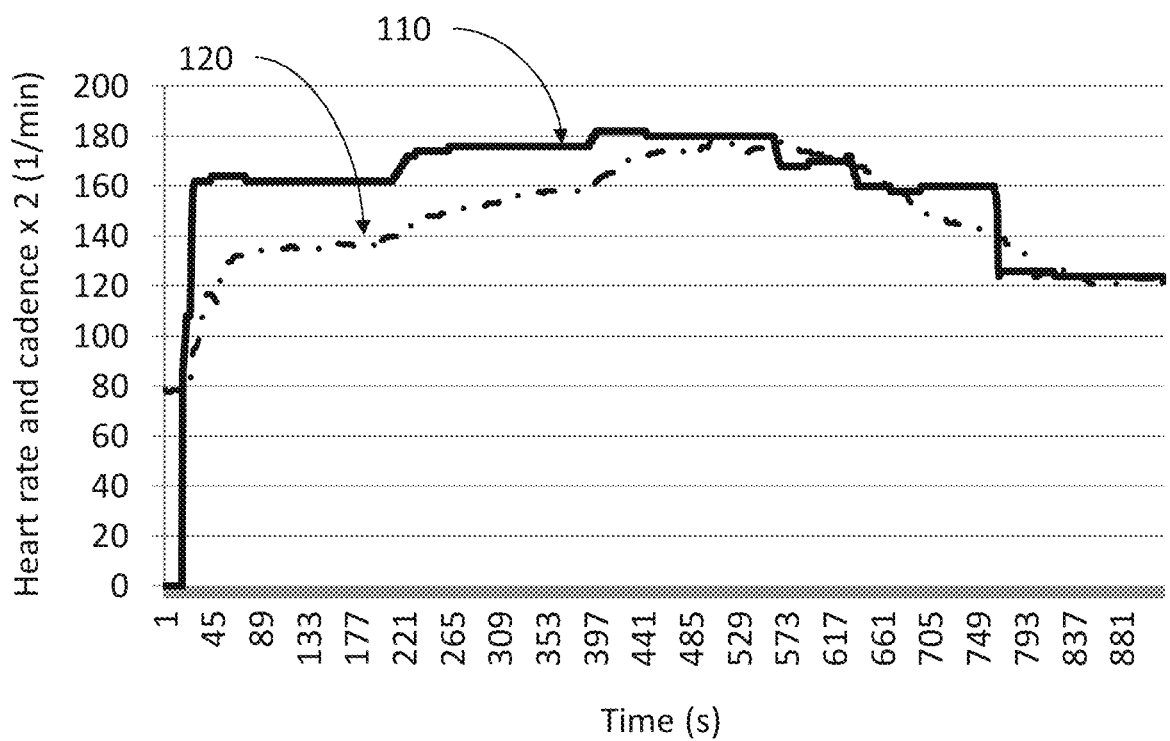
FIG. 1B shows a graph of a runner's heart rate and cadence on the vertical axis and time on the horizontal axis.

FIG. 1A a runner 100A taking rhythmic steps 110A, i.e. moving forward with a relatively stable cadence. FIG. 1B shows real heart rate data 120 and cadence data 110 measured from a running performance (cadence multiplied by two to get "both feet frequency"). It can be seen that as the performance proceeds and the cadence takes its maximum value (about 180 1/min), the heart rate 120 approaches the cadence 110, the two quantities having in the end approximately the same values. Thus, there is a relation between cadence and heart rate.

According to one embodiment, the present invention takes advantage of this relation by calculating at least one correlation factor dependent on temporal characteristics of periodic features of the heartbeat signal (heartbeats) compared with temporal characteristics of periodic features in the acceleration signal (e.g. steps, revolutions). Mutual temporal comparison of the characteristic features in this way is used to calculate at least one performance parameter depicting intensity of said sports performance and/or fitness level of the person.

Figure 2:
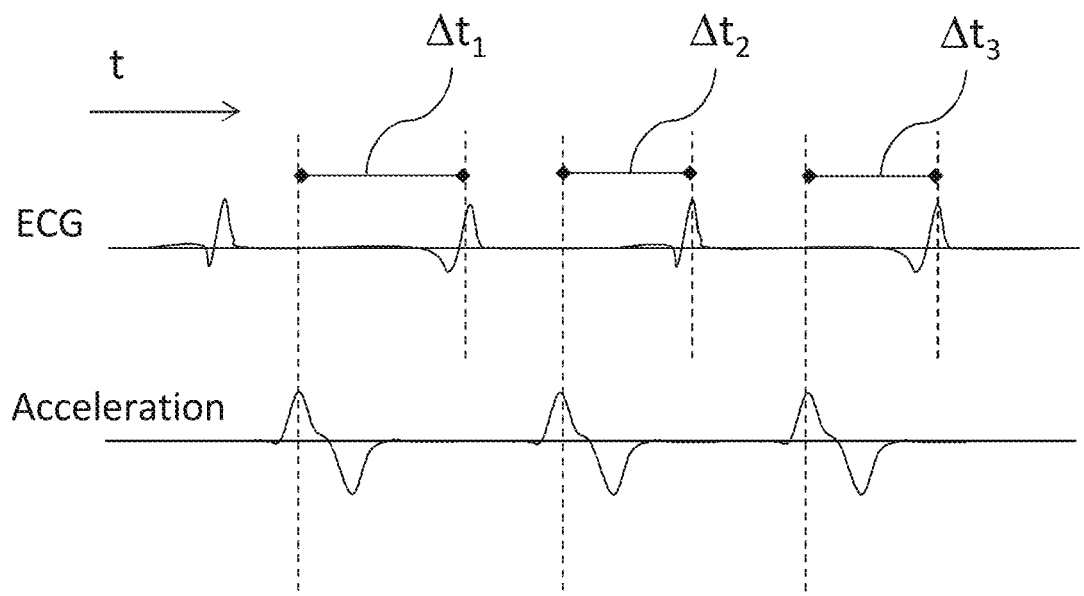
FIG. 2 shows parallel schematic graphs of ECG and acceleration signals to illustrate correlation-based temporal analysis of the signals.

FIG. 2 illustrates one method of making the mutual comparison using an artificial ECG signal (upper) and acceleration signal (lower) forms. From each signal, peaks are detected and their time points are recorded, i.e. the peaks are time stamped. Then the elapsed time $\Delta_{t1}$, $\Delta_{t2}$, $\Delta_{t3}$ between each acceleration peak and the next heartbeat peak is calculated based on corresponding time stamps. Then, it is determined whether the durations $\Delta_{t1}$, $\Delta_{t2}$ and $\Delta_{t3}$ are essentially equal or not, or potentially or reflect a systematic trend. At the anaerobic threshold, the time differences between the time stamped peaks, i.e. $\Delta_{t1}$, $\Delta_{t2}$ and $\Delta_{t3}$, approach a constant value. Suitable statistical methods and figures can be used to evaluate the behavior of the time differences.

Instead of peaks, the detection can be based on some other characteristic features of the signals, depending on the intended use. In particular, for the acceleration signal, different detection algorithms may be necessary for different sports and/or different location of the acceleration sensor, in order to obtain the cadence in a reliable way.

Taking the deduction made above with reference to FIG. 2 even farther, if it is know that the acceleration signal is measured at a heart rate belt (and therefore gives peak at every step) and the durations $\Delta_{t1}$, $\Delta_{t2}$ and $\Delta_{t3}$ are statistically equal, it can be concluded that the step and heart rate are equal and that the person is working at or close to his/her anaerobic threshold. On the other hand, the durations are systematically changing in one direction or the other, it can be estimated how far below or above the anaerobic threshold the person is working at. The knowledge on the deviation from the anaerobic threshold can be used together with heart rate and/or cadence and/or speed data in further estimations on the intensity of the performance or the fitness level of the person.

The performance parameter can in particular comprise anaerobic heart rate threshold level of the person determined by detecting or estimating the heart rate level at which the heart rate and stepping frequency are equal or the heart rate is a multiple of stepping frequency. In running, this means the condition that cadence multiplied by two equals the heart rate is satisfied. The parameter may also comprise deviation from anaerobic heart rate threshold level determined by detecting or estimating the heart rate level at which the periodicities of the heart rate and the acceleration are equal and determining the difference between the present heart rate level and the anaerobic heart rate threshold level determined. The outcome may also be a derivative of threshold level or deviation therefrom, i.e. another quantity calculated at least partly using the estimated threshold level or deviation.

The performance parameter can also comprise maximum step length or maximum speed in the aerobic range. In this embodiment, the step length of the person is determined using suitable means (e.g. acceleration-based foot pod measurement, combined acceleration and GPS measurements or user-given parameter). Then, the maximum speed $v_{anaer}$ that the person is able to maintain for a long period equals $$2*cadence*step\_length. \quad (1)$$

This can further be used to calculate back the maximum step length or to estimate maximum oxygen intake and further fitness level of the person. For example maximum oxygen intake $VO_{2,max}$ is obtained using the formula $$A*v_{anaer}+B, \quad (2)$$

where A and B are predetermined constants. Then using $VO_{2,max}$ and the age and sex of the person, one can robustly estimate the fitness level of the person among a population with methods known per se.

According to one embodiment, the maximum step length or maximum speed in the aerobic range and/or anaerobic threshold heart rate are used as scaling factors in heart rate based energy consumption determination. Thus, the equipment can self-calibrate its energy consumption determination based on the fitness-related data obtained by means of the invention. These scaling factors can be used not only in characterizing running, but also other sports, after being determined on the basis of a running performance.

FIG. 2 is given to exemplify one potential method only in a simplified way using artificial signal forms. In practice, a longer inspection period would be needed to make reasonable conclusions on the relation between the cadence and heart rate and deviation from the anaerobic threshold. It is appreciated that the same information can be obtained using other correlation-based methods or through frequency analysis.

Figure 9:
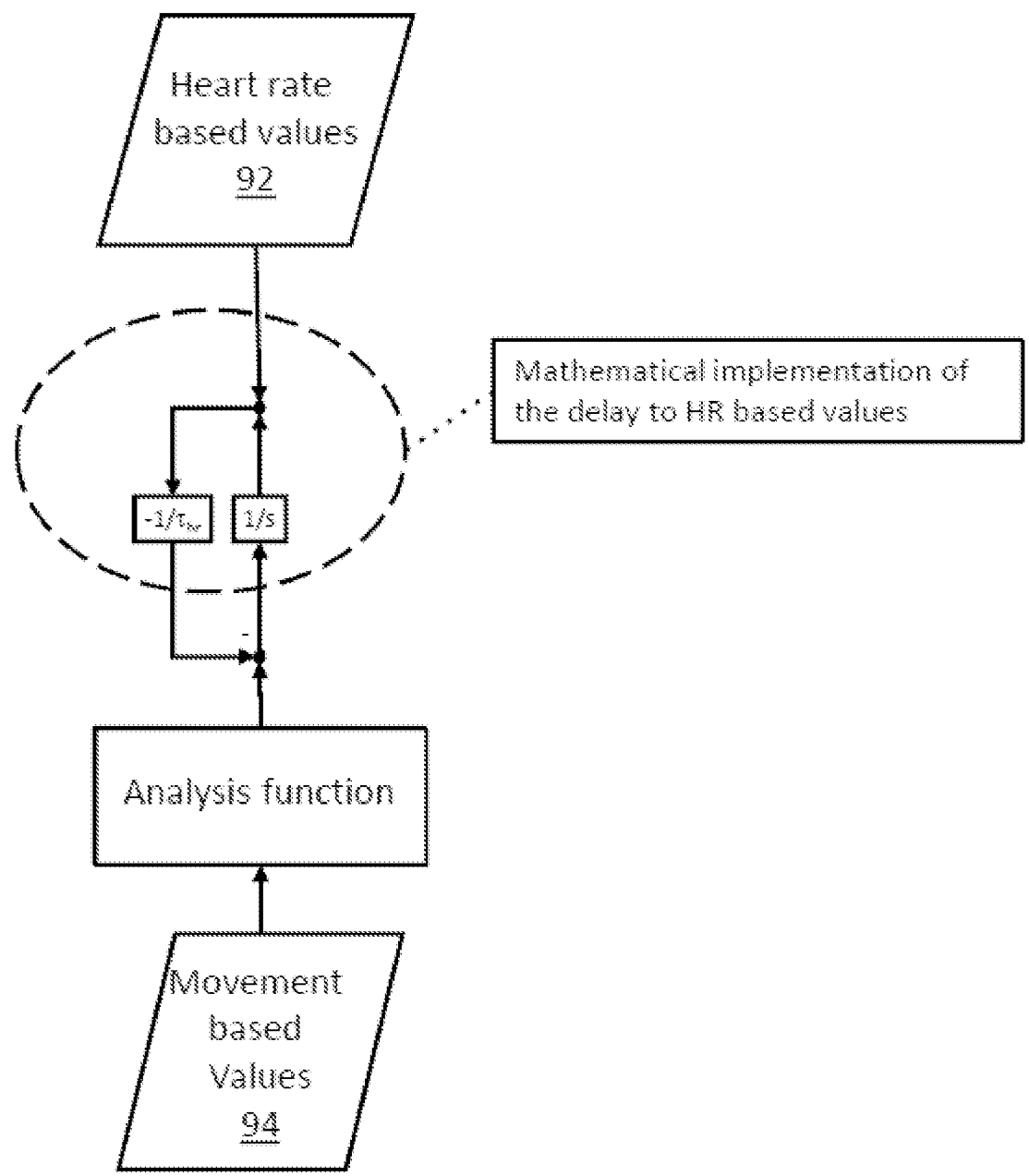
FIG. 9 illustrates as a flow chart how persons heart rate related parameters can be linked to physical movement parameters introducing a time delay element in between the two domains according to one embodiment.

Heart rate of a person typically follows changes in the intensity of physical performance with a delay. Therefore, performances that contain a lot of physical intensity changes are challenging as concerns heart rate and physical parameter comparisons. FIG. 9 illustrates how heart rate related parameters 92 can be linked to physical movement parameters 94 introducing a time delay element $\tau_{hr}$ in between. This enables real time calculation of performance parameters using either or both the heart rate and movement signals at all times. The time delay element $\tau_{hr}$ describes the difference of response times of physical measurement and heart rate measurement to the intensity of the performance.

Figure 10:
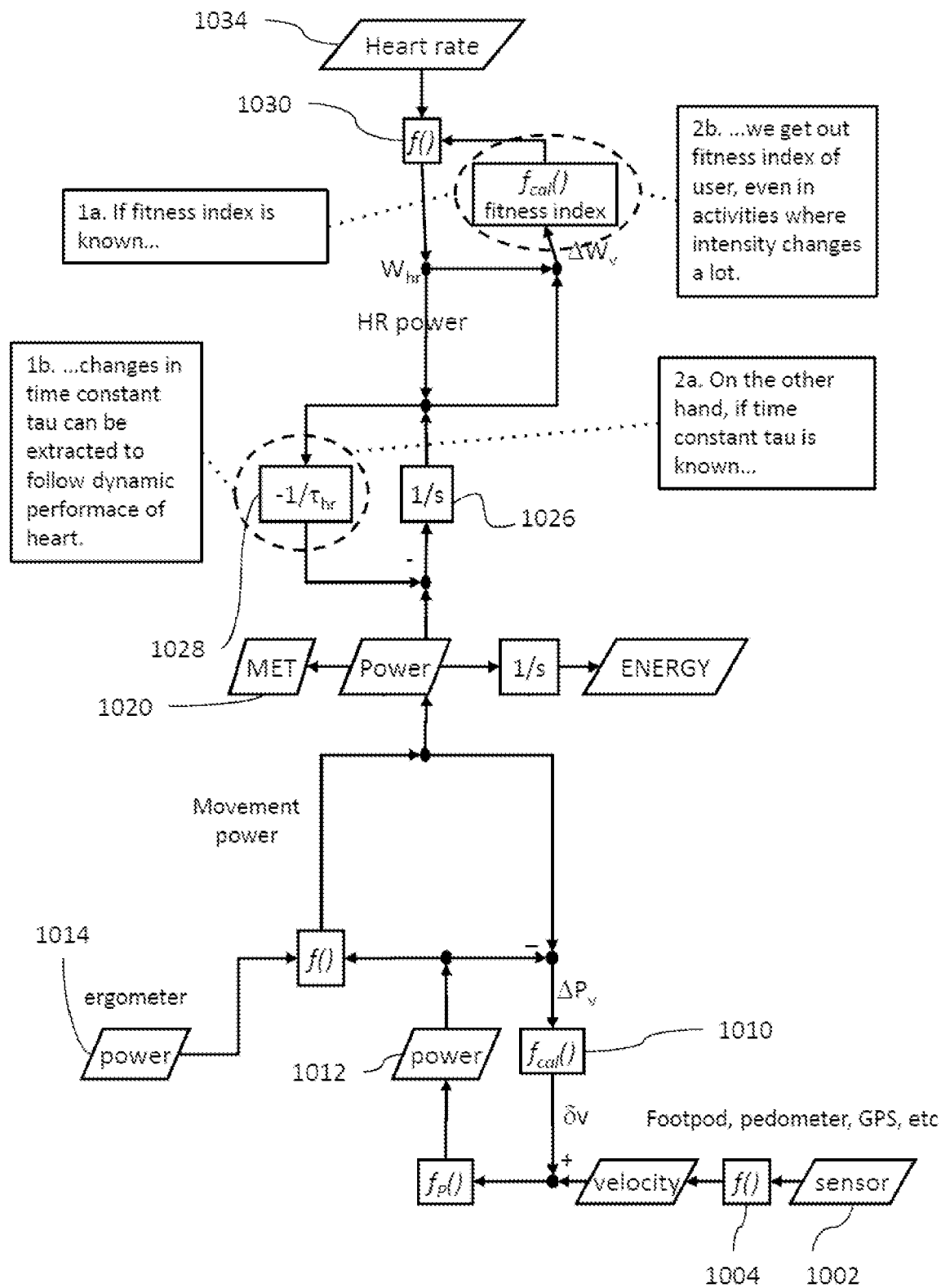
FIG. 10 illustrates as a flow chart how the different power estimates from intensity and heart rate based sensor sources are connected together according to one embodiment.

As a more detailed example, FIG. 10 shows how power estimations using heart rate and moment data are linked together with this method. Mathematically this link can be formulated in the form of differential equation $$\begin{bmatrix} \dot{P}_{Movement} \\ \dot{P}_{hr} \end{bmatrix} = \begin{bmatrix} 0 & 0 \\ 1/\tau_{hr} & -1/\tau_{hr} \end{bmatrix} \begin{bmatrix} P_{movement} \\ P_{hr} \end{bmatrix} \quad (3)$$

where $P_{movement}$ is the power estimate based on physical movement data, $P_{hr}$ is power estimate based on heart rate signal, and $\tau_{hr}$ is the parameter describing the time delay between heart rate response and physical movement based intensity change. Changes in $\tau_{hr}$, relative to resting condition $\tau_{hr\_rest}$, correlate with real time EPOC. Therefore $\tau_{hr}$ describes person's fatigue level in real time, without any need for prior exercise history data. Function $$EPOC = f(\tau_{hr}, \tau_{hr\_rest}) \quad (4)$$

that is used for EPOC calculation, can be for instance partial linear model that is formed based on test database data. The process of FIG. 10 thus enables estimation of EPOC value and fatigue of person from intensity changes or in the reverse case to calculate fitness index at all times even during the intensity changes.

In more detail, FIG. 10 shows how one can determine energy consumption 1024 and/or metabolic equivalent of task (MET) 1020 starting from data provided by a motion sensor 1002 and heart rate sensor 1034, an optional power sensor 1014. In the process the motion sensor data from different sensor sources, for instance footpod speed, wrist accelerometer, gps speed, bike pod speed, or bikepod power sensor data, is always transformed to motion based power 1012 through functions implemented in 1004. Since we can have multiple motion sources they can be used to calibrate other sensor through the function 1010.

Power that person produces can be also calculated from heart rate data. However, since the heart rate adjusts with delay to intensity level changes, this delay must be taken into account in the system. Part 1026 of the system and especially time constant tau Dir in function 1028 presents models the delay properties of the human heart relative to motion based data. In this particular implementation of the system model there are two variables that can be allowed to change, fitness index in function 1030 and time constant tau Dir in function 1028. The system model can change these values in order to make the heart rate power equal to motion power. When there are small changes in motion power, that is in sport intensity level, then the system model adjusts more strongly the fitness index so that the heart rate and motion based powers are equal. Thus, the system determines the user's fitness index. On the other hand, when there are a lot of intensity changes, fitness index is changed less and the system model adjusts more the time constant tau $\tau_{hr}$. As described earlier, changes in time constant tau $\tau_{hr}$ during the performance give the fatigue level and thus EPOC of the user.

In some cases the value and behavior of time constant tau $\tau_{hr}$ is known, for instance when user is fully rested prior to the performance and has done an orthostatic heart rate test.

Then the fitness index of the user can be calculated accurately and quickly even in activities where the intensity changes a lot, for instance in hockey, soccer, badminton, tennis, floor ball, etc.

Figure 3:
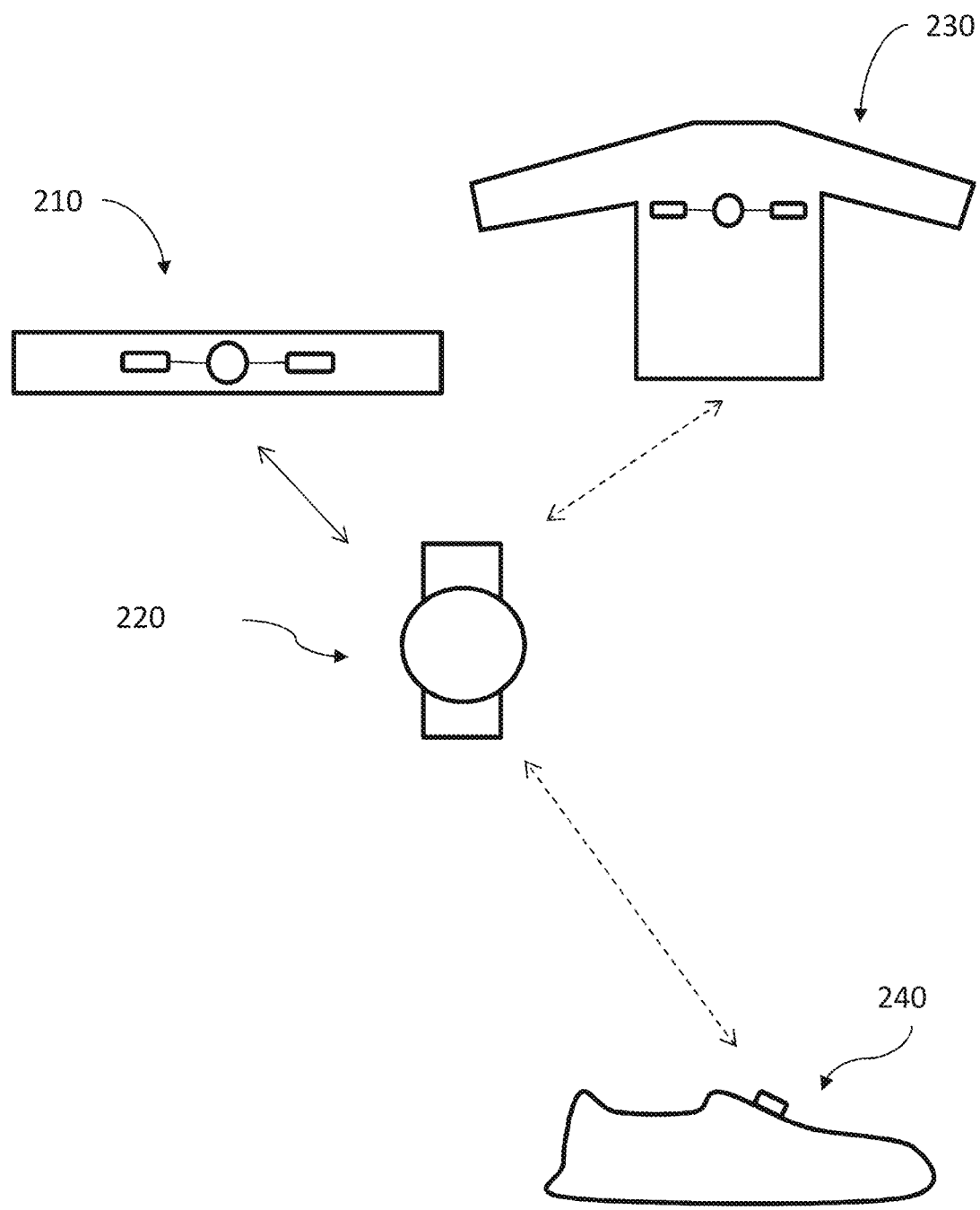
FIG. 3 shows a schematic view of a system according to one embodiment of the invention and some optional components and variations thereof.

FIG. 3 shows a system with a wristop computer 220 as a data storage and/or visualization device and a heart rate belt 210 as a data-collecting and processing device. The heart rate belt comprises an ECG sensor and an electronic module that reads and processes the signal provided by the ECG sensor. An acceleration sensor is provided either in the heart rate belt 210 or the wristop computer 220, or both. The heart rate belt 210 is in wireless communication with the wristop computer.

Alternatively to a heart rate belt 210, a smart garment 230 can be used, providing the same functionality as the heart rate belt 210 discussed above.

In a still further embodiment, there is provided an additional unit in the system, such as a sensor unit attached to a shoe 240 of the sportsman. The additional sensor unit may comprise an acceleration sensor providing the acceleration signal and is in wireless communication with the heart rate belt 210 or smart garment 230 and/or the wristop computer 220 to provide the acceleration signal or data derived therefrom for further processing or use.

It should be noted that the wristop computer can be replaced with any other wearable device, such as another wearable sports tracking unit or mobile phone capable of communicating with other components of the system.

Wireless communication of data between separate devices of a multi-device equipment takes place advantage of a wireless radio-frequency transmitter-receiver or transceiver-transceiver pair. The wireless communication protocol can be one used for communication between computers, and/or between any remote sensors, such as a Bluetooth LE or the proprietary ANT+ protocol. These are using direct-sequence spread spectrum (DSSS) modulation techniques and an adaptive isochronous network configuration, respectively. Enabling descriptions of necessary hardware for various implementations for wireless links are available e.g. from the Texas Instrument®'s handbook "Wireless Connectivity" which includes IC circuits and related hardware configurations for protocols working in sub-1-and 2.4-GHz frequency bands, such as ANT™, Bluetooth®, Bluetooth® low energy, RFID/NFC, PurePath™ Wireless audio, ZigBee®, IEEE 802.15.4, ZigBee RF4CE, 6LoWPAN, Wi-Fi®.

Figure 4A:
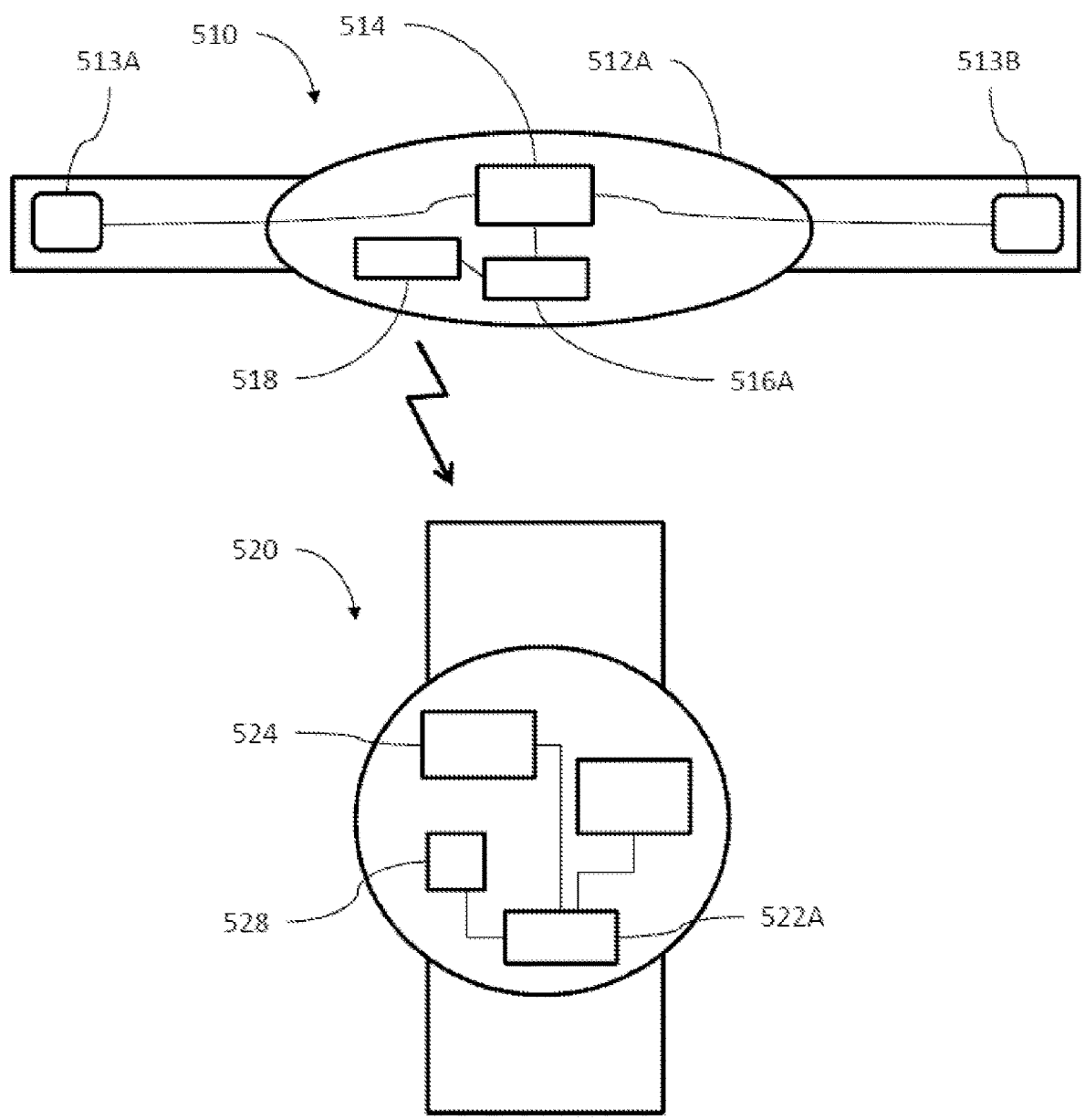
FIG. 4A shows a block diagram of a heart rate belt and a wristop device according to one embodiment of the invention.

FIG. 4A depicts one preferred implementation of the system in more detail. There is provided a heart rate belt 510 with a pair of ECG electrodes 513A, 513B connected to an ECG signal preprocessor 514 (typically including at least an A/D converter) contained in an integral or removable electronics module 512A. The ECG data obtained from the preprocessor is processed in digital form in a processing unit 516A running an algorithm for finding the individual heartbeats and optionally further the heart rate. The processing unit 516A can also provide time stamps for the heartbeats. The heartbeat data, i.e., the heartbeats, corresponding time stamps and/or the heart rate, are wirelessly communicated to a wristop computer 520 via a radio transmitter unit 518 in the belt 510 and radio receiver unit 524 in the wristop computer. The receiver unit 524 is functionally connected to a processing unit 522A. In addition, there is provided an acceleration sensor 528 in the wristop computer functionally connected to the processing unit 522A.

The processing unit 522A is configured to analyze the heartbeat data (heart beat pulses, time stamps or heart rate) received from the heart rate belt 510 and acceleration data from the acceleration sensor 528 to find their temporal correlation, for example using one of the methods described above in more detail. The processing unit 522A also calculates the desired performance parameter using the correlation information.

The processing unit 522A may also be configured to execute software for determining the type of sports based on the acceleration signal and for determining energy consumption using an algorithm and source(s) of information (ECG and/or acceleration) depending on the sports type determined. Alternatively or in addition to automatic sports type determination, the processing unit may be configured to read a stored sports type parameter, typically given by the user or previously automatically determined, from a memory (not shown) of the device and to use that for selecting an appropriate algorithm and source(s) of information. Exemplary methods for automatic sports type determination are described elsewhere in this document.

Figure 4B:
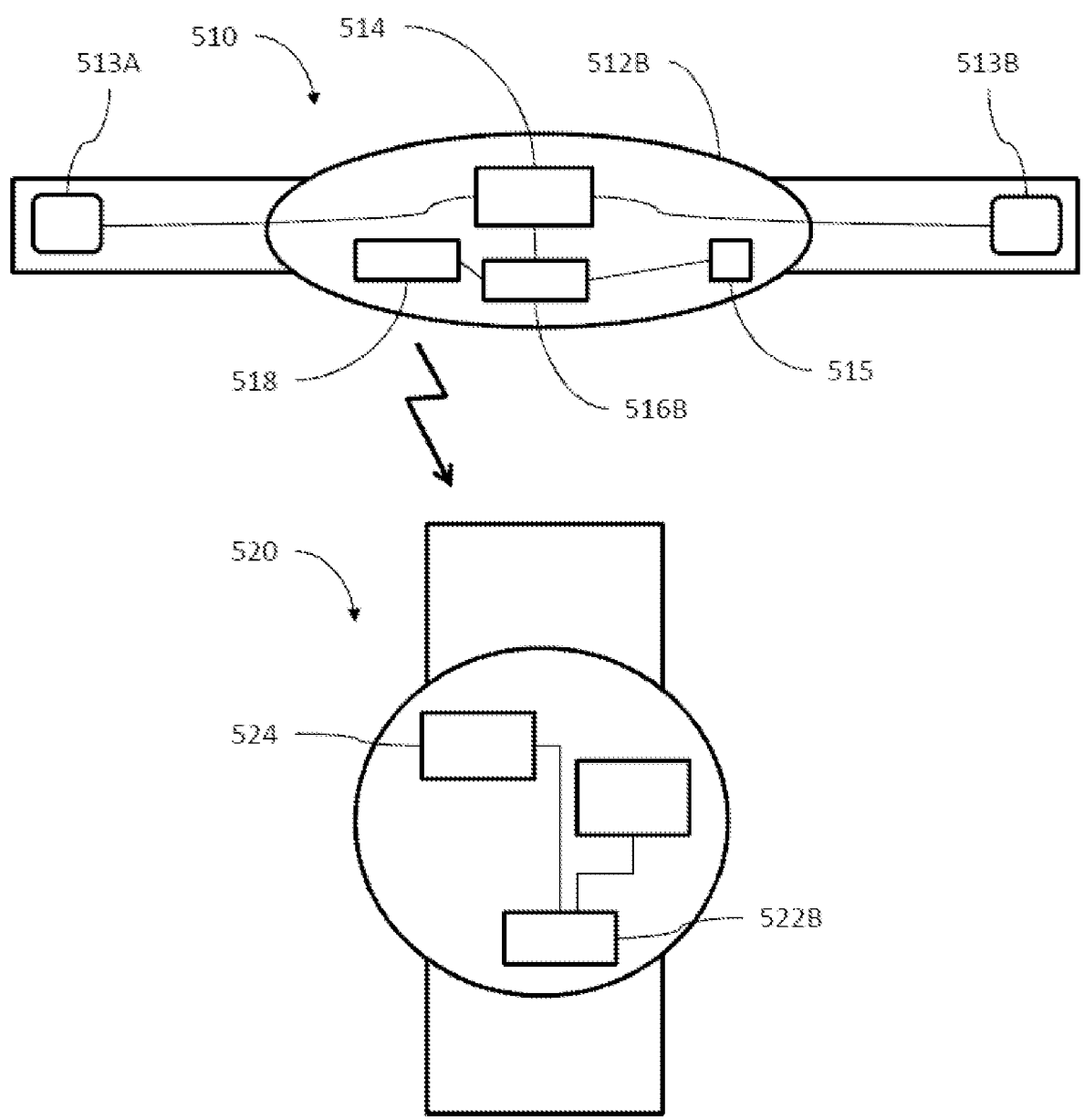
FIG. 4B shows a block diagram of a heart rate belt and a wristop device according to an alternative embodiment of the invention.

FIG. 4B shows an embodiment mostly similar to that of FIG. 4A but having an acceleration sensor 515 in the electronics module 512B of the heart rate belt. The processing unit 516B is configured to read the acceleration signal from the acceleration sensor 515. The processing unit 516B may also carry out one or more of the functions of the processing unit 516A described above and to additionally process the acceleration signal correspondingly to find repetitive movements or movement frequency. The processing unit 516B may also determine the type of sports based on the acceleration signal and to communicate the type, along with the ECG and/or acceleration data, to the wristop computer, which then runs the energy consumption algorithm in its processing unit 522B. According to a second variant, the processing unit 516B of the heart rate belt 510 is also configured to analyze the temporal correlation of the heartbeat and acceleration signals and optionally to determine the desired performance parameter. Likewise, it may also run the energy consumption algorithm either partially or entirely. As an example of partial calculation, energy consumption per a mass unit can be determined based on the heartbeat data or acceleration data in the heart rate belt and then this is multiplied with the user mass in the wristop computer having an interface for inputting the user mass. In one embodiment, the communication interface between the devices allows for transmission of data to the heart rate belt, whereby also the mass information can be sent and utilized in the heat rate belt to obtain a user-specific energy consumption value.

Figure 5:
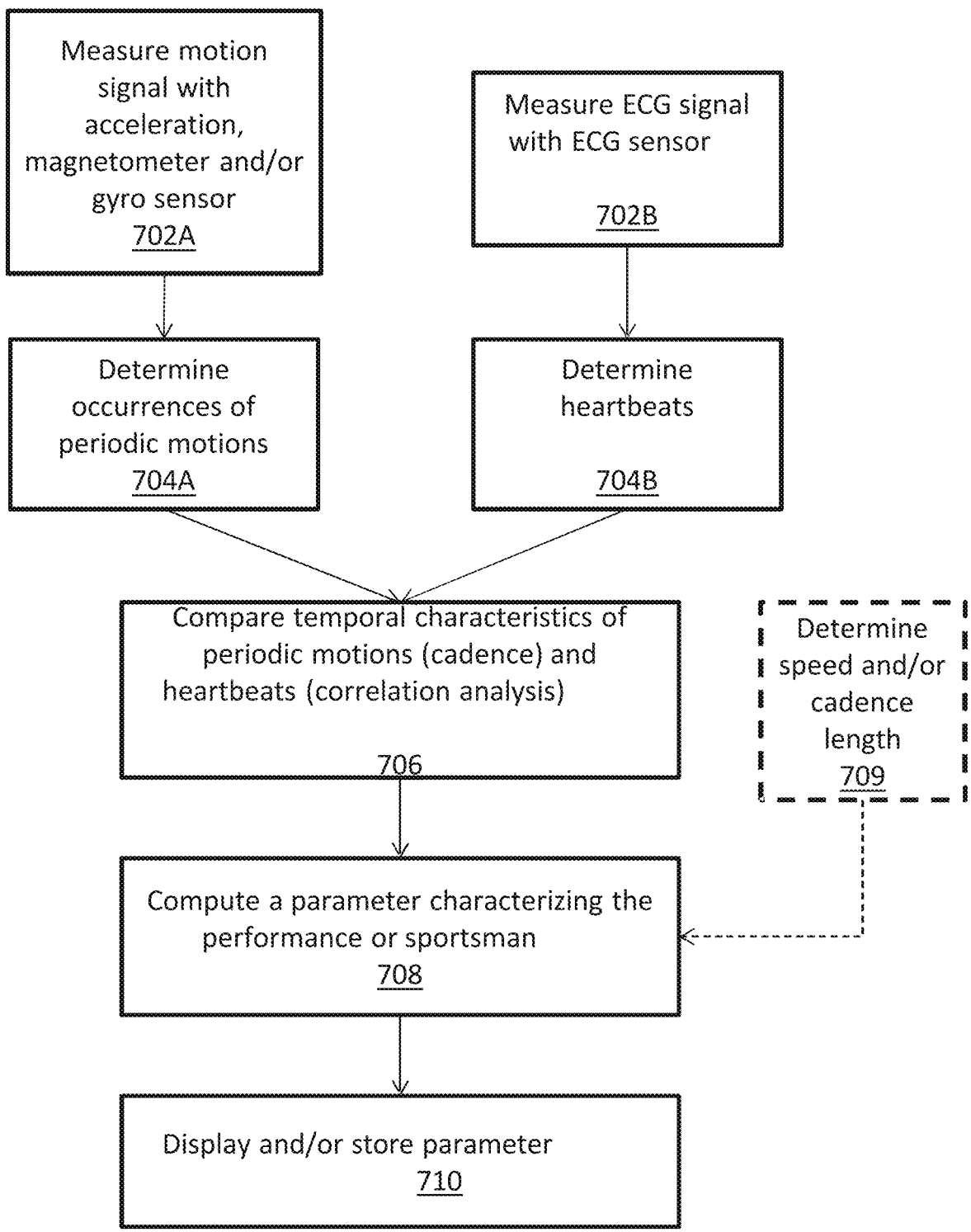
FIG. 5 shows a flow chart of the method according to one embodiment of the invention.

FIG. 5 shows a flow chart of the present method according to one embodiment. The motion signal is measured using an accelerometer, magnetometer and/or gyro in step 702A and the ECG signal with an ECG sensor simultaneously in a parallel step 702B. The signals are then processed in steps 704A and 704B to determine periodic motions and heartbeats, respectively. The temporal characteristics of the periodic motions and heartbeats are then compared in step 706 to find their potential correlation. If the motions and heartbeats are in synchronization, i.e. their frequencies are equal or one is a multiple of the other, there is full correlation (there may well be a phase shift between the periodic frequencies). A correlation factor of some kind is derived to describe the frequency difference. Then, based on the correlation factor, the desired parameter of interest is calculated in step 708 and displayed and/or stored in step 710.

According to one embodiment particularly suitable for monitoring running or cycling performances, speed and/or cadence length information is additionally utilized to determine the performance parameter. This option is illustrated with dashed in FIG. 5 as lines as step 709 providing additional input to the computation step 708. Speed can be obtained directly using data from a position sensor, such as a satellite positioning sensor, or velocimeter, such a cyclometer, being part of the system, or using e.g. known or measured step (running) or revolution (cycling) length and the cadence obtained from the motion sensor. Step length can also be approximated using the sensor data obtained from the accelerometer, magnetometer or gyro.

According to one embodiment, the computing means is programmed to estimate energy consumption of the person during the performance using the heartbeat and/or motion signals. In particular, the equipment may comprise means for determining the type of the sports performance and the computing means for calculating the energy consumption parameter are adapted to utilize the heartbeat signal, the motion signal or both signals in combination in different manner depending on the type of the sports performance determined. The type of the sports performance can be determined either manually by the user but even more advantageously automatically.

According to one preferred embodiment, the device is capable of distinguishing the sports based on physical rhythmicity, i.e. similarity and temporal stability of successive similar movements, required in particular sports. For example, street or track running is physically very rhythmic sports, i.e. involves a stabile cadence, whereas tennis is more impulsive and irregular. The proposed solution can robustly distinguish between these kinds of sports and apply a corresponding algorithm for calculating energy consumption, which utilize at least partly different sources of information. Energy consumption of running may be better characterized by cadence and tennis by heart rate characteristics. Automatic type determination based on the stability of cadence is also capable of distinguishing between street or track running and cross county running or orienteering, which involve kinematically and/or temporally more versatile motion and in which energy consumption is usually better characterized by heart rate.

According to one embodiment, there are provided means for receiving and storing a user-specified sports performance type parameter in a memory of the equipment. This is called manual type determination. In addition, the means for determining the type of the sports performance are adapted to read said user-specified sports performance type parameter from said memory in order to determine the type of the sports performance. The means for receiving and storing may comprise user interface means and associated software and hardware means in a wristop computer or mobile phone part of the present system. If necessary, the performance type parameter can be communicated to a heart rate belt or some other unit where energy consumption calculations are carried out.

According to one embodiment, the means for determining the type of the sports performance are adapted to determine the type of the sports performance automatically based on characteristics, in particular rhythmicity, of the motion signal. According to a further embodiment, this is implemented such that the means for determining the type of the sports performance are adapted to calculate a parameter depicting rhythmicity of the performance based on the motion signal and the device is adapted to use that parameter for determining the type. In one approach, the means for calculating the energy consumption parameter are adapted to utilize only the ECG signal in calculations if the rhythmicity of the performance is below a predefined level and only the motion signal if the rhythmicity of the performance is above the predefined level. Thus, rhythmic sports are characterized by the acceleration data, for example and irregular sports by the heart rate data, allowing for more accurate estimations for energy consumption.

According to one option, the means for determining the type of the sports performance are adapted to determine rhythmicity of the motion signal by detecting repeating features in the motion signal, associating time stamps to the repeating features, and calculating correlation between intervals between successive time stamps, preferably at all sensor axes. Correlation value per axis forms characterization vector that is utilized to differentiate between types of sports. Such correlation analysis can be implemented in a wearable device efficiently in the time domain.

In an alternative option, the means for determining the type of the sports performance are adapted to apply Fourier analysis on the motion signal to determine rhythmicity of the motion signal. Discrete Fourier analysis can also be relatively efficiently implemented in small devices.

Figure 6:
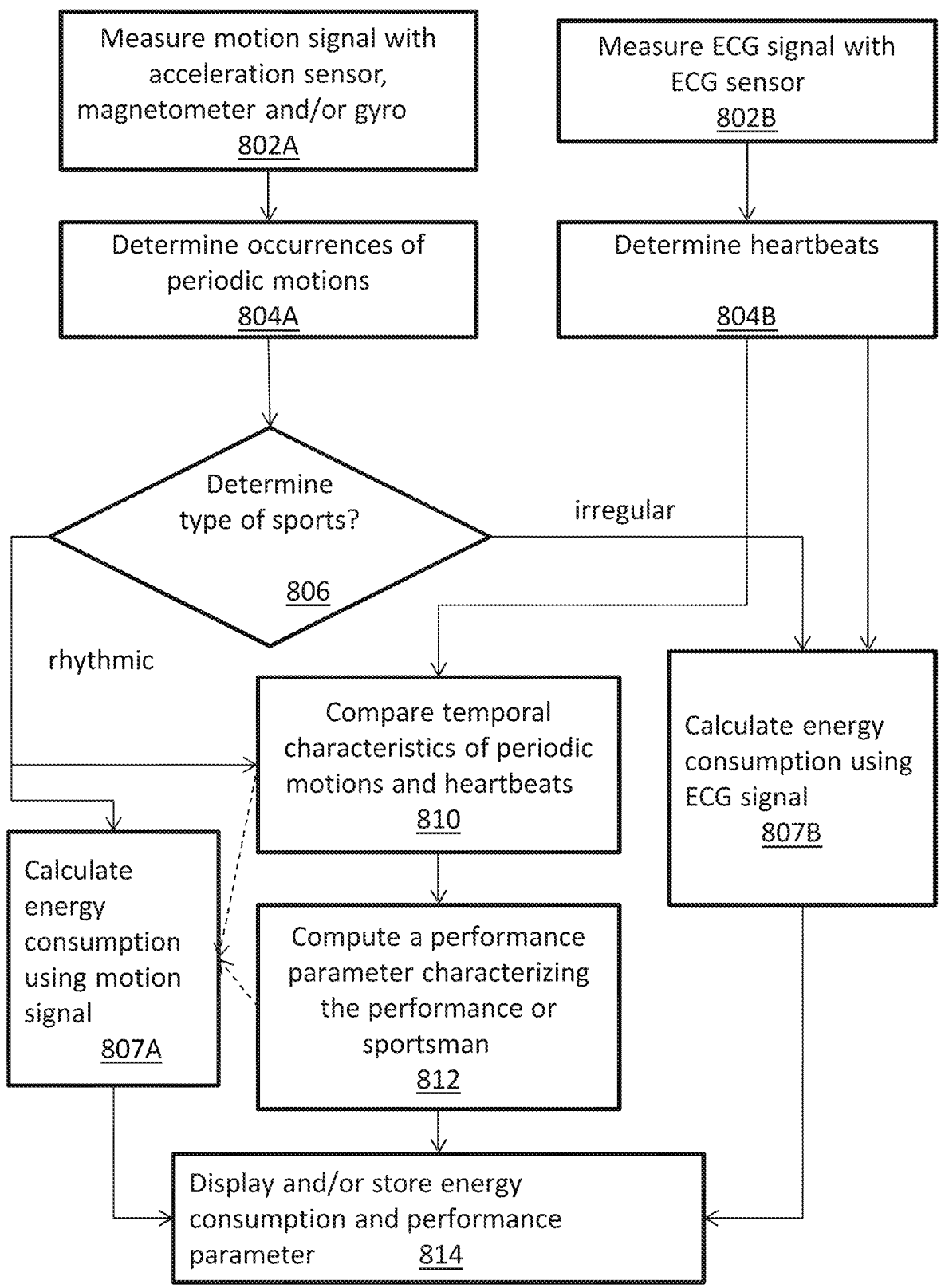
FIG. 6 shows a flow chart of the method according to an alternative embodiment of the invention additionally comprising a sports type determination phase.

FIG. 6 shows an embodiment otherwise similar to that illustrated in FIG. 5 but having additional sports type determination. The motion and ECG signals are measured in steps 802A, 802B and used for motion and heartbeat detection in steps 804A, 804B, respectively. The motion data is further used in step 806 for determining the type of the sports being performed. Methods for this are described elsewhere in this document in more detail. If the sports type is "rhythmic", it makes sense to continue with temporal comparison of the motion and heartbeat data in step 810 and to characterize the performance based on the comparison in step 812. In addition, energy consumption is calculated using or putting more weight on the motion signal in step 807A. If the sports is irregular by nature, the comparison phase is skipped and energy calculated on the basis of the heartbeat signal in step 807B. The results of the calculations are displayed and/or stored in step 814.

The dashed lines in FIG. 6 indicate that the result of temporal comparison of the motion and heartbeat signals (step 810) or the parameter derived based on the comparison (step 812) can also be used in the energy consumption calculation (step 807A). Thus, the deviation from the anaerobic threshold and therefore different metabolic states can be taken into account. This is, however, optional since in certain rhythmic sports, such as running, the energy consumption can also relatively accurately be determined based on the motion data only.

According to one embodiment, for determining the type of sports, the motion signal is analyzed so as to detect cyclic, i.e. regular, motion characteristic to a cyclic sports, such as running, in it. Rhythmicity can be determined in the time domain for example by time stamping impulses detected in the signal using correlation analysis to determine whether the inter-impulse interval remains constant (to a predefined degree) over time, which would be indicative of a performance of regular nature. If the correlation between intervals is low, the performance is irregular. In an alternative embodiment, the motion based sensor signal is converted to frequency domain using a discrete Fourier transformation, and the presence of strong (peaked) frequency components is detected. There is a peak in the frequency data if a lot of cyclic motion takes place at constant frequency over a chosen time interval. The rhythmicity determination may be carried out continuously or repeated at predefined intervals during the performance so that the energy consumption algorithm can be changed, if the type of sports changes. This can occur for example if the user carries out gymnastic exercises every now and then during a jog.

As concerns the energy consumption part, the determination of the type of sports can have more than two outcomes (not just between rhythmic and irregular), and there may be more than two algorithms corresponding to these outcomes implemented.

According to one embodiment, it is determined if the user has specified a particular sports type manually (and wishes that to be used as a basis for algorithm selection). In the affirmative, the algorithm is chosen accordingly without automatic determination. In the negative, automatic type determination is initiated, as described above.

The rhythmicity analysis should be carried out over a time period of significant length, so that random and occasional variations in the frequency of motion or measurement errors do not result in a wrong outcome. If the rhythmicity stays relatively constant over the period chosen, a first algorithm is chosen for further calculations and on the opposite case a second algorithm is chosen.

In a still further embodiment, the computing unit is programmed to filter out movement-induced components of the heartbeat signal based on the motion signal for providing a filtered heartbeat signal and to use to filtered signal for deriving the performance parameter. This embodiment solves the problem of generation of movement-induced repeating errors in the heartbeat signal. In particular at the beginning of a performance, when the measurement electrodes of the measurement device and also the skin is dry, variations in the contact pressure between the electrodes and the skin due to cadence result in measurement artifacts. For the same reason, also static electricity may accumulate close to the electrodes and cause undesired peaks in the signal measured.

Figure 7:
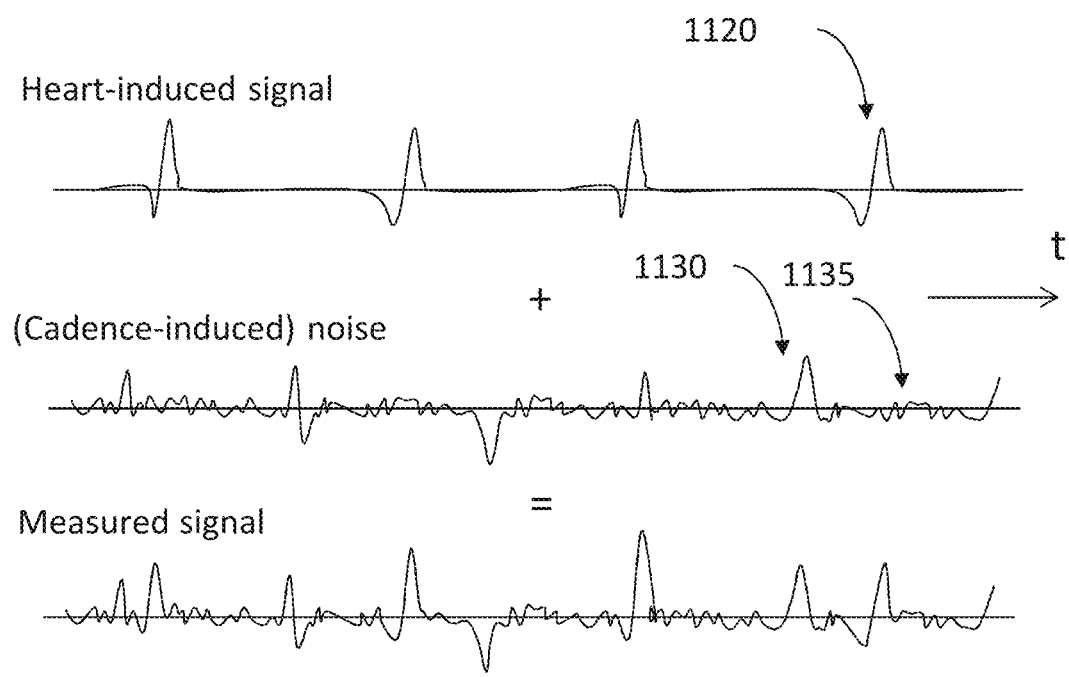
FIG. 7 shows schematic graph of formation of a measured ECG signal by heartbeat-induced signal and cadence-influenced noise.

FIG. 7 illustrates ECG signal formation. In an ideal case, the heartbeat of a runner, for example, produces a clean ECG signal with easily detectable heartbeat waveforms 1120 as illustrated by the uppermost graph of FIG. 7. However, in practice, there is always random noise 1135 present, as well as systematic noise, i.e., artifacts 1130 induced by the movement of the runner. In the case of rhythmic cadence, the artifacts are typically repeated periodically, following the more or less constant rhythm of the movement. The random noise 1135 and artifacts 1130 are illustrated by the middle graph of FIG. 7. Thus, the real measured signal contains the sum of the real heartbeat signal and the noise and artifact signals, which is illustrated by the lowermost graph of FIG. 7. From this sum signal, it is much more difficult to detect the heartbeats robustly than from the ideal ECG signal.

According to one embodiment, the computing unit is programmed to filter out frequency components from the heartbeat signal that are common to the motion signal and the heartbeat signal. Preferably, this is carried out in the frequency domain by computing a Fourier transform of the heartbeat signal and a Fourier transform of the motion signal and suppressing frequency components of the muscular activity signal that correspond to some or all of the frequency components of the motion signal.

Preferably, the heartbeat sensor and the motion sensor are located in the same device unit, such as a heart rate belt or smart garment. This ensures that the motion signal corresponds to actual movement of the heartbeat sensor. It is however possible that the sensors are located in different device units potentially located on different body parts, because their rhythmic movements are typically not independent and therefore sufficient information for removing rhythmic artifacts can be obtained.

Figure 8:
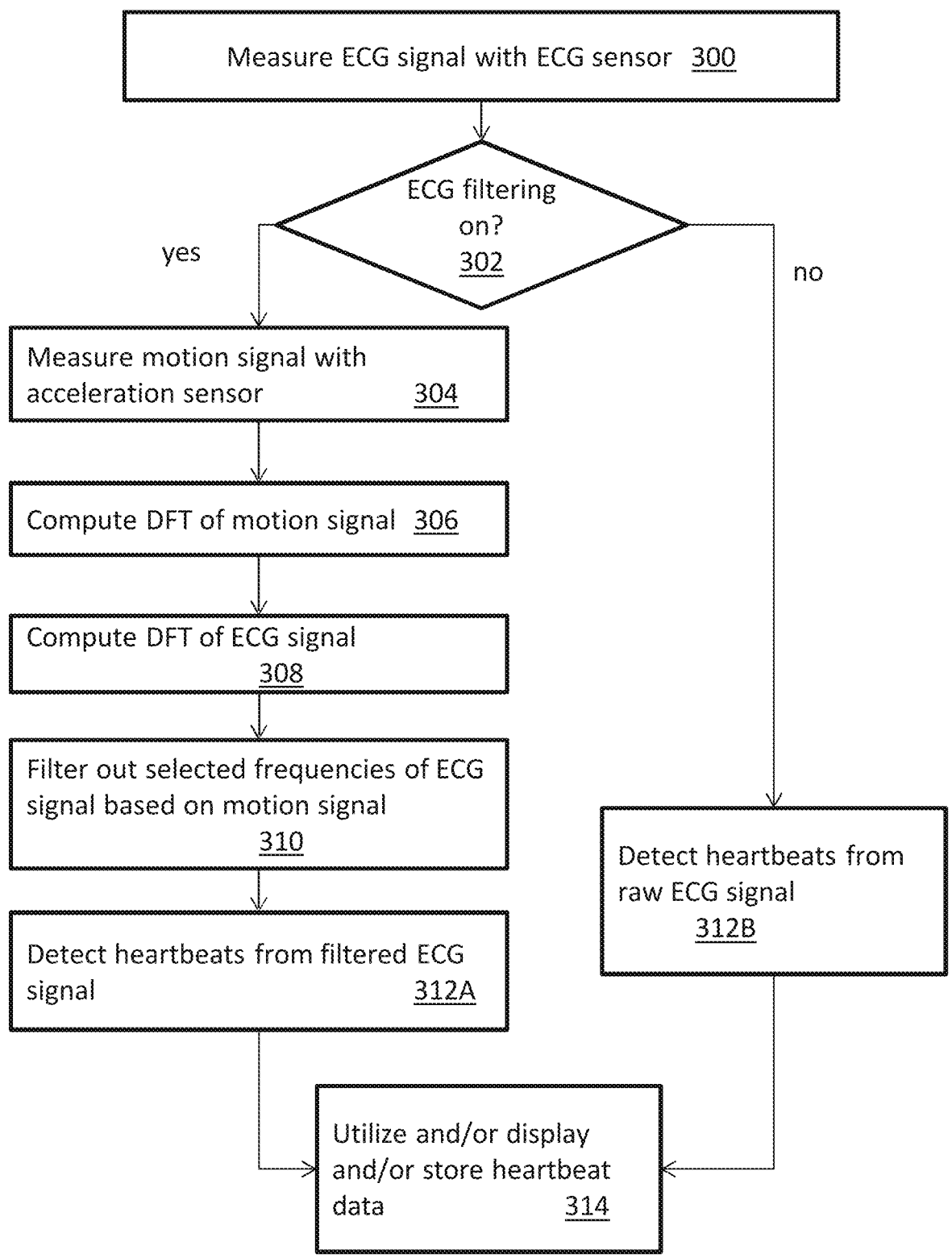
FIG. 8 shows a flow chart of filtering the heartbeat signal based on motion signal according to one embodiment of the invention.

FIG. 8 shows one exemplary flow schematic for signal filtering. The heartbeat raw signal is measured in step 300 from a suitable location of the body of the person using a suitable sensor. In step 302, it is checked whether rhythmic filtering feature of the system has been activated. If not, the heartbeats or muscular activities are detected in step 312B based on the raw signal using a suitable algorithm, which are known per se. If the filtering is set active, motion signal is measured in step 304 to assist in the filtering process. A discrete Fourier transform (DFT) of the motion signal is computed in step 306, preferably using a suitable fast Fourier transformation algorithm. The same is carried out for the heartbeat signal in step 308. The DFT of the motion signal indicates the frequencies at which there may be motion-induced artifacts present in the heartbeat signal. Some or all of these frequencies are then suppressed from the heartbeat signal, preferably in the frequency domain to provide a filtered heartbeat signal in step 310. Individual heartbeats are then detected using the filtered signal in step 312A. In step 314, the results of the detection are then utilized in further computations to characterize the sports performance or the person and/or stored in a memory of the system and/or visualized. Typical uses of the heartbeat data include energy consumption estimation and training effect estimation.

The steps of the FIG. 8 can naturally take place in any suitable order, which may deviate from the one illustrated. Moreover, if the present signal cleaning method is set to take place by default, steps 302 or 312B are not needed.

It is to be understood that the embodiments of the invention disclosed are not limited to the particular process steps, units, components, devices, materials or products disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, various embodiments and examples of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the description, numerous specific details are provided, such as examples of shapes and dimensions etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A wearable electronic equipment for monitoring a sports performance and determining the fitness level of a person, comprising:
a heartbeat sensor configured to measure a heartbeat signal in response to heartbeat of the person;
a motion sensor configured to measure a motion signal in response to movement of the person; and
at least one processor within the wearable electronic equipment functionally connected to the heartbeat sensor and the motion sensor, said processor configured to:
determine the fitness level of the person by detecting periodic features in the measured heartbeat signal and in the measured motion signal,
determining a temporal correlation between said periodic features, and
calculating, based at least partly on said temporal correlation, at least one performance parameter depicting said fitness level of the person, wherein said at least one performance parameter comprises:
an anaerobic heart rate threshold level of the person determined by detecting or estimating a frequency of the measured heartbeat signal at which said periodic features of the measured heartbeat signal and said periodic features of the measured motion signal are equal, or
a derivative from said anaerobic heart rate threshold level of the person determined by detecting or estimating a frequency of the measured heartbeat signal at which said periodic features of the measured heartbeat signal and said periodic features of the measured motion signal are equal, or
a deviation from said anaerobic heart rate threshold level of the person determined by detecting or estimating a frequency of the measured heartbeat signal at which said periodic features of the measured heartbeat signal and said periodic features of the measured motion signal are equal, said deviation determined from a difference between a current heart rate level and said determined anaerobic heart rate threshold level, or
a derivative of said deviation from said anaerobic heart rate threshold level of the person determined by detecting or estimating a frequency of the measured heartbeat signal at which said periodic features of the measured heartbeat signal and said periodic features of the measured motion signal are equal, said deviation determined from a difference between a current heart rate level and said determined anaerobic heart rate threshold level, or
any combination thereof,
wherein the wearable electronic equipment comprises
at least one displayless electric heart rate module integral with or functionally connectable with a heart rate belt or a smart garment having integral heart rate measurement electrodes so as to form said heartbeat sensor, and the module comprising said motion sensor and at least part of said processor, and
at least one wristop computer or mobile handheld device configured to establish wireless communication with the electric heart rate module and being provided with a display configured to visualize said performance parameter.

2. The wearable electronic equipment according to claim 1, wherein the processor is further configured to:
calculate at least one correlation factor, said correlation factor being dependent on the temporal characteristics of periodic features of the measured heartbeat signal compared with the temporal characteristics of periodic features in the measured motion signal, and
using said correlation factor, calculate said at least one performance parameter.

3. The wearable electronic equipment according to claim 1, wherein the processor is further configured to calculate at least a parameter depicting intensity of the performance, strain of the performance, fatigue of the person, said fitness level of the person or a combination thereof as said at least one performance parameter.

4. The wearable electronic equipment according to claim 1, wherein the at least one performance parameter comprises at least one of an index, a fitness index, a fatigue index, an energy consumption, or a combination of at least one of: said index, said fitness index, said fatigue index, or said energy consumption.

5. The wearable electronic equipment according to claim 1, wherein the processor is further configured to calculate at least a maximum speed and/or step length of the person in an aerobic range as said at least one performance parameter.

6. The wearable electronic equipment according to claim 1, wherein the processor is further configured to calculate the performance parameter based on a difference between the measured heartbeat signal and a frequency of said periodic features of the measured motion signal.

7. The wearable electronic equipment according to claim 1, wherein the processor is further configured to:
associate first time stamps with individual heartbeats detected from said measured heartbeat signal,
associate second time stamps with periodic features detected from said measured motion signal,
based on said first and second time stamps, detect and/or estimate a heartbeat frequency at which a temporal difference in the periodicities of the measured heartbeat signal and periodicities of said measured motion signal remain constant over a plurality of periods of the signals, and
calculate a performance parameter based on said detected and/or estimated heartbeat frequency.

8. The wearable electronic equipment according to claim 1, wherein the processor is further configured to calculate a Fourier transformation of the measured heartbeat and motion signals, and to compare characteristics of the measured signals in a frequency domain in order to calculate said performance parameter.

9. The wearable electronic equipment according to claim 1, wherein said at least one performance parameter further comprises an index number proportional to a ratio of a cadence of the movement of the person based on said measured motion signal and the heart rate of the person, based on said measured heartbeat signal.

10. The wearable electronic equipment according to claim 1, further comprising a position sensor configured to obtain speed data of the person, and wherein said processor is further configured to utilize said speed data in order to calculate said performance parameter.

11. The wearable electronic equipment according to claim 1, wherein the processor is further configured to determine an average step length of the person and wherein said processor is further configured to utilize said average step length when calculating the performance parameter.

12. The wearable electronic equipment according to claim 11, wherein the processor is further configured to at least:
read a step length as a user-input parameter from a memory unit of the equipment,
determine a step length based on the motion signal, or
determine the average step length based on the combination of the periodic features of the measured motion signal and the speed data obtained using a position sensor.

13. The wearable electronic equipment according to claim 1, further comprising an electric heart rate module integral with or functionally connectable with a heart rate belt or a smart garment having integral heart rate measurement electrodes so as to form said heartbeat sensor, said electronic heart rate module including said motion sensor.

14. The wearable electronic equipment according to claim 13, wherein the electric heart rate module further comprises the processor.

15. The wearable electronic equipment according to claim 1, wherein said heartbeat sensor comprises an electrical ECG sensor, an optical sensor, a pressure sensor or an acceleration sensor.

16. The wearable electronic equipment according to claim 1, wherein the motion sensor is at least one of: an accelerometer, a magnetometer, or a gyroscope.

17. A method for monitoring a sports performance and determining the fitness level of a person, comprising the steps of:
obtaining a heartbeat signal by measuring the person's heartbeat using a wearable heartbeat sensor;
obtaining a motion signal by measuring movement of the person using a wearable motion sensor; and
in one or more computing units functionally connected to the wearable heartbeat sensor and the wearable motion sensor:
detecting periodic features in the heartbeat signal and in the motion signal;
determining a temporal correlation of the periodic features of the heartbeat signal and the motion signal; and
calculating, using at least one processor comprised within said one or more computing units, at least one performance parameter depicting said fitness level based at least partly on said temporal correlation,
wherein said at least one performance parameter comprises:
an anaerobic heart rate threshold level of the person determined by detecting or estimating a frequency of the heartbeat signal at which said periodic features of the heartbeat signal and said motion signal are equal, or
a derivative from said anaerobic heart rate threshold level of the person determined by detecting or estimating a frequency of the heartbeat signal at which said periodic features of the heartbeat signal and said motion signal are equal, or
a deviation from said anaerobic heart rate threshold level of the person determined by detecting or estimating a frequency of the heartbeat signal at which said periodic features of the heartbeat signal and said motion signal are equal, said deviation determined from a difference between a current heartbeat signal and said anaerobic heart rate threshold level, or
a derivative of a deviation from said anaerobic heart rate threshold level of the person determined by detecting or estimating a frequency of the heartbeat signal at which said periodic features of the heartbeat signal and said motion signal are equal, said deviation determined from a difference between a current heartbeat signal and said anaerobic heart rate threshold level, or
any combination thereof,
wherein the at least one processor is configured to cause the calculated performance parameter depicting said fitness level of the person to be displayed on at least one of: a wearable electronic equipment and a mobile phone.

18. The method according to claim 17, wherein the at least one performance parameter comprises at least an intensity of the performance, strain of the performance, fatigue of the person, said fitness level of the person or a combination thereof.

19. The method according to claim 17, wherein the at least one performance parameter further comprises an index number proportional to a ratio of cadence of the movement of the person and a heart rate of the person, based on said measured motion signal and said measured heartbeat signal, respectively.

20. A method for optimizing the intensity of a sports performance of a person, comprising the steps of:
   obtaining a heartbeat signal by measuring the person's heartbeat using a wearable heartbeat sensor;
   obtaining a motion signal by measuring movement of the person using a wearable motion sensor; and
   in one or more computing units functionally connected to the wearable heartbeat sensor and the wearable motion sensor:
      detecting periodic features in the heartbeat signal and in the motion signal;
      determining a temporal correlation of the periodic features of the heartbeat signal and the motion signal; and
      calculating, using at least one processor comprised within said one or more computing units, at least one performance parameter depicting the intensity of the sports performance,
   wherein said at least one performance parameter is calculated based at least partly on said temporal correlation and wherein said at least one performance parameter comprises:
      an anaerobic heart rate threshold level of the person determined by detecting or estimating a frequency of the heartbeat signal at which said periodic features of the heartbeat signal and the motion signal are equal, or
      a derivative from an anaerobic heart rate threshold level of the person determined by detecting or estimating a frequency of the heartbeat signal at which said periodic features of the heartbeat signal and the motion signal are equal, or
      a deviation from an anaerobic heart rate threshold level of the person determined by detecting or estimating a frequency of the heartbeat signal at which said periodic features of the heartbeat signal and the motion signal are equal, said deviation determined from a difference between a current heartbeat signal and said anaerobic heart rate threshold level, or
      a derivative of a deviation from an anaerobic heart rate threshold level of the person determined by detecting or estimating a frequency of the heartbeat signal at which said periodic features of the heartbeat signal and said motion signal are equal, said deviation determined from a difference between a current heartbeat signal and the anaerobic heart rate threshold level, or
      any combination thereof,
   wherein the at least one processor is configured to cause the calculated performance parameter depicting the intensity of the sports performance to be displayed on at least one of: a wearable electronic equipment and a mobile phone, and wherein the detecting or estimating of the frequency of the heartbeat signal at which said periodic features of the heartbeat signal and the motion signal are equal comprises:
      detecting peaks from the heartbeat signal and from the motion signal,
      recording the timestamps of the detected peaks,
      calculating an elapsed time between each motion signal peak and a next heartbeat signal peak, and
      determining, if the calculated elapsed times are essentially equal, or if the calculated elapsed times reflect a systematic trend, in order to detect or estimate said frequency of the heartbeat signal at which said periodic features of the heartbeat signal and the motion signal are equal.

* * * * *